United States Patent [19]
Hess et al.

[11] Patent Number: 5,861,007
[45] Date of Patent: *Jan. 19, 1999

[54] ADAPTIVE SEARCH AV AND AUTO PVARP ADAPTATION TO SAME WITH ADDITIONAL BENEFIT

[75] Inventors: Michael F. Hess, Minneapolis; H. Toby Markowitz, Roseville; James W. Busacker, St. Anthony, all of Minn.

[73] Assignee: Medtronic, Inc.

[*] Notice: This patent issued on a continued prosecution application filed under 37 CFR 1.53(d), and is subject to the twenty year patent term provisions of 35 U.S.C. 154(a)(2).

[21] Appl. No.: 806,302

[22] Filed: Feb. 26, 1997

Related U.S. Application Data

[63] Continuation of Ser. No. 536,602, Sep. 29, 1995, abandoned.

[51] Int. Cl.[6] ............................................. A61N 1/362
[52] U.S. Cl. ............................................................ 607/9
[58] Field of Search ................................. 607/9, 17, 27

[56] References Cited

U.S. PATENT DOCUMENTS

| | | | |
|---|---|---|---|
| 4,091,817 | 5/1978 | Thaler | 607/9 |
| 4,284,082 | 8/1981 | Funke et al. | 607/9 |
| 4,554,920 | 11/1985 | Baker, Jr. et al. | 607/25 |
| 5,085,215 | 2/1992 | Nappholz et al. | 607/25 |
| 5,144,950 | 9/1992 | Stoop et al. | 607/9 |
| 5,282,838 | 2/1994 | Hauser et al. | 607/9 |
| 5,318,594 | 6/1994 | Limousin et al. | 607/9 |
| 5,334,220 | 8/1994 | Sholder | 607/9 |
| 5,507,782 | 4/1996 | Kieval | 607/9 |

*Primary Examiner*—William E. Kamm
*Assistant Examiner*—George R. Evanisko
*Attorney, Agent, or Firm*—Harold R. Patton; Michael B. Atlass

[57] ABSTRACT

An AV search method and apparatus is taught with some variation described. It allows a pacemaker to find the appropriate AV interval so as to avoid pacing in the ventricle when it is not necessary, even if there is intermittent AV conduction in the patient. Also, an adaptive PVARP method and apparatus is disclosed that allows the PVARP and AV interval to be adjusted together automatically.

7 Claims, 6 Drawing Sheets

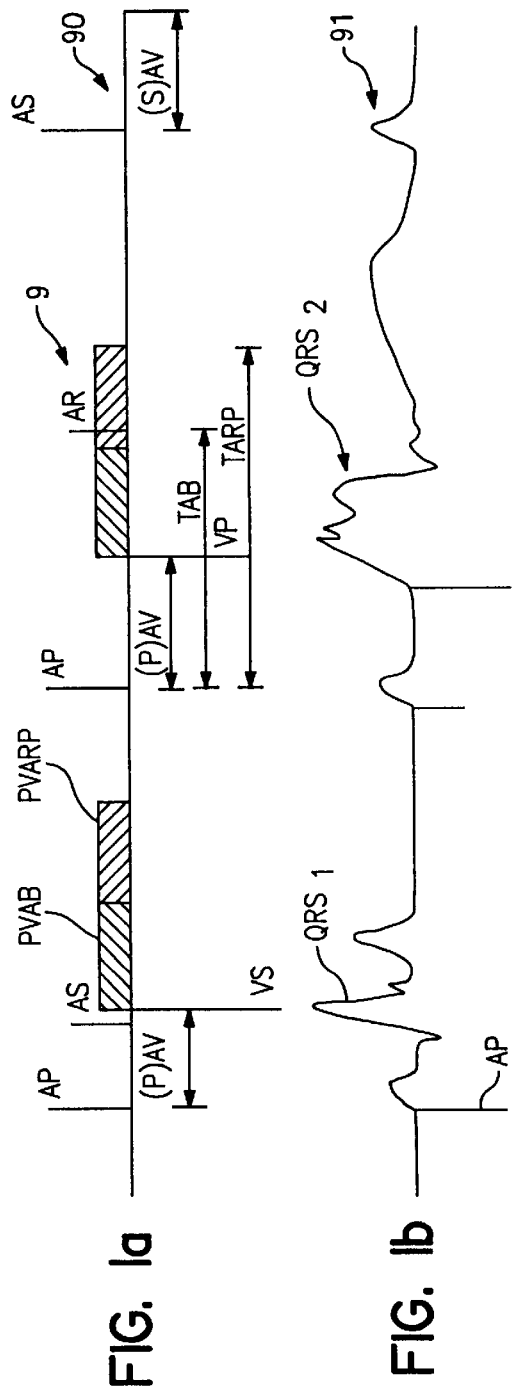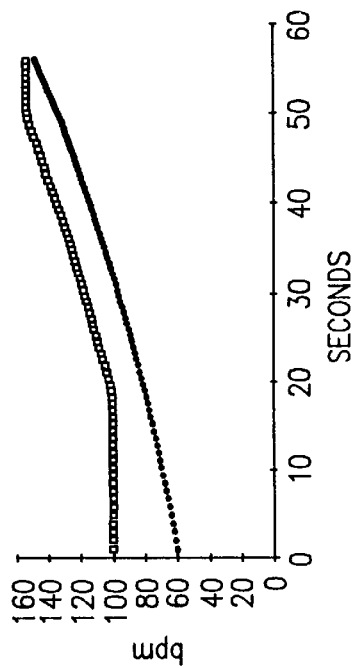
FIG. 1a
FIG. 1b
FIG. 7

ADAPTIVE SEARCH AV AND AUTO PVARP ADAPTATION TO SAME WITH ADDITIONAL BENEFIT

This application is a continuation of application Ser. No. 08/536,602 filed on 29th Sep. 1995 now abandoned.

This invention relates to adjustments made to the timing of specific pacemaker monitored intervals, particularly the AV interval and the PVARP or PVAB. (Definitions: AV=AtrioVentricular, or the time between the beginning of an atrial event and the beginning of the next and probably dependent ventricular event, PVARP=Post Ventricular Atrial Refractory Period, that is, the time the pacemaker considers sensing events in the atrium after a ventricular pace as non-events, and PVAB=Post Ventricular Atrial Blanking period, i.e. the period of time after a pace that there is no sensing at all in the atrium. TARP=Total Atrial Refractory Period, TAB=Total Atrial Blanking period, SAV=the AV interval used after an atrial sensed event, as contrasted with a PAV which=the AV interval used after a paced atrial event.)

The indication for changing the length of the AV interval is primarily rate adaptive pacing.

Rate adaptive pacers which follow a patient's physiologic demand have been available for some time. Recent examples include U.S. Pat. No. 5,271,395 (Wahlstrand et al.), U.S. Pat. No. 4,856,524 (Baker, Jr.) which use an AV interval timer instead of an activity sensor (as in U.S. Pat. No. 5,052,388 to Sivula et al.), and one which uses minute ventilation (as in U.S. Pat. No. 5,271,395 Wahlstrand) to determine the appropriate pacing rate. Adjusting AV intervals to be different for atrial synchronous verses atrial ventricular sequential pacing has been taught in U.S. Pat. No. 4,421,116 issued to Markowitz. Also, shortening AV intervals to be delivered after an atrial pacing pulse for DDI mode pacing was shown in Levine et al., U.S. Pat. No. 5,417,714.

Pacemaker technology has been around for some 30 years. The technology for implanting such hermetically sealed electrical pulse generators (usually with batteries for power) responsive to a patient's pacing needs are well known in many aspects and those will not be described with particularity here. Instead, the reader should refer to descriptions available in the art cited in this application and other readily available literature.

An AV interval is important to maintain for AV block patients. AV block means that an event in such a patient's atrium will not propagate into the ventricle, and thus the ventricles must be artificially paced. The AV interval is used to time such an artificial ventricular pacing pulse. A particularly problematic situation exists in intermittent AV block patients, since the opportunity for natural conduction will be prevented by having an AV interval that is shorter than the natural one. This problem manifests in rate adaptive pacing because the length of the AV interval should be (and is) adjusted shorter as the rate increases in order to promote efficient cardiac hemodynamics. Further complications can develop where the patient has a shortened AV to promote hemodynamics to compensate for Hypertropic obstructed CardioMyopathy(HOCM). In general, it has been suggested in an article by Bailey, et al, (article 188, X World Con.) that an automated AV interval adjustment could be used to maintain ventricular capture or to prevent ventricular pseudofusion. Also, some complications develop where the pacing device depends on an adjusting AV interval for also adjusting the PVARP.

Other relevant thinking in this area includes at least, an article on different beneficial AV intervals for sensed and paced atrial events for DDD pacing, (Alt, et al., J. of Electrophysiology, Vol.1 No.3, 1987, pp250–56), A patent (U.S. Pat. No. 5,024,222) on automatic adjustment to AV and escape intervals issued to Thacker, and one (U.S. Pat. No. 4,108,148) issued to Cannon, which called for automatically adjusting the AV interval using a p wave triggered monostable multivibrator.

To be able to rate adjust the AV interval and PVARP together in a way that is different for patients that need adjustments based on HOCM AV adjustment therapy and/or intermittent AV block is not something currently available in a pacemaker system. The atrial tracking behavior of a pacemaker at high rates is defined by the upper tracking rate interval time value and the sum of the AV interval and the time of the PVARP. Traditionally, changes to the AV interval on an ambulatory basis for preservation of AV conduction or optimization for HOCM patients would alter this behavior at high rates as the changes have not been coordianted with the value of PVARP or the pacemaker's upper rate.

Other adjustments can also be made which are described in reference to alternate preferred embodiments herein.

BRIEF DESCRIPTION OF THE DRAWINGS

FIGS. 1a and 1b are paired marker channel and surface ECG diagrams.

FIG. 7 is a graph of heart rate vs time showing the 2:1 block point vis-a-vis atrial rate.

DETAILED DESCRIPTION OF PREFERRED EMBODIMENTS

First a description of the pacemaker system follows.

Figure 2:
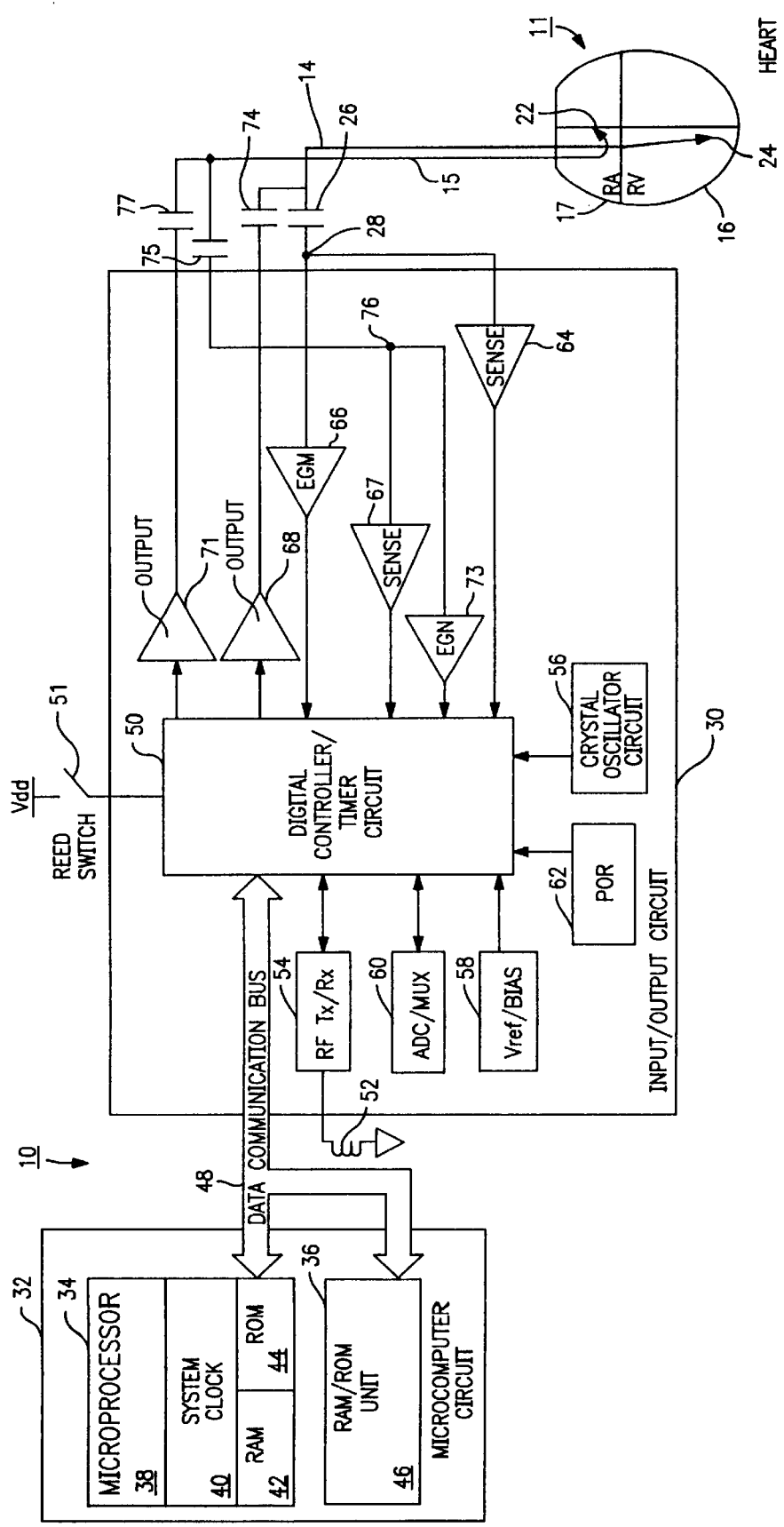
FIG. 2 is a block diagram schematic of an implantable pulse generator (IPG or pacemaker) that may be used with preferred embodiments of this invention.

FIG. 2 is a block circuit diagram illustrating one possible form of a pacemaker 10 capable of carrying out the present invention. Although the present invention is described in conjunction with a microprocessor-based architecture, it is understood that it could be implemented in other technology such as digital logic-based, custom integrated circuit (IC) architecture, analog circuits, etc., if desired. It is also understood that the present invention may be implemented in cardioverters, defibrillators and the like.

Preferred embodiments would use two leads, 14, 15. Lead 14 includes an electrode 24 located near its distal end positioned within the right ventricle 16. Electrode 24 is coupled by a lead conductor 14 through an input capacitor 26 to the node 28, and to the input/output terminals of an input/output circuit 30. Lead 15 has a distal electrode positioned within the right atrium 17. Electrode 22 is coupled by a lead conductor 15 through an input capacitor 75 to a node 76, and to the input/output terminals of the input/output circuit 30.

Input/Output Circuit 30 contains the operating input and output analog circuits for digital controlling and timing circuits to detect electrical signals derived from the heart, such as the cardiac electrogram (EGM or ECG). It also receives output from sensors (not shown but which may be connected to the leads 14 and 15), and it is the part which applies stimulating pulses to the heart under the control of software-implemented algorithms in a Microcomputer Circuit 32.

Microcomputer Circuit 32 has an On-Board Circuit 34 and an Off-Board Circuit 36. On-Board Circuit 34 includes a microprocessor 38, a system clock 40, and on-board RAM 42 and ROM 44. Off-Board Circuit 36 includes an off-board RAM/ROM Unit 46. Microcomputer Circuit 32 is coupled by Data Communication Bus 48 to a Digital Controller/Timer Circuit 50. Microcomputer Circuit 32 may be fabricated of custom IC devices augmented by standard RAM/ROM components. The computation and running of the algorithmic processes described below occur within this circuit area generally, based on signals from the rest of the IPG. all the variables defined in terms of value are preferably stored and updated within this circuit 32.

It will be understood by those skilled in the art that the electrical components represented in FIG. 2 are powered by an appropriate implantable-grade battery power source (not shown).

An antenna 52 is connected to Input/Output Circuit 30 for purposes of uplink/downlink telemetry through a radio frequency (RF) Transmitter/Receiver Circuit (RF TX/RX) 54. Telemetering both analog and digital data between antenna 52 and an external device, such as an external programmer (not shown), is accomplished in the preferred embodiment by means as substantially described in U.S. Pat. No. 5,127,404, issued on Jul. 7, 1992, entitled "Telemetry Format for Implantable Medical Device", incorporated herein by reference. A reed switch 51 is connected to Input/Output Circuit 30 to enable patient follow-up via disabling the sense amplifier 146 and enabling telemetry and programming functions, as is known in the art.

A Crystal Oscillator Circuit 56, typically a 32,768 Hz crystal-controlled oscillator, provides main timing clock signals to Digital Controller/Timer Circuit 50. Most timing periods depend on a clock to turn on or off under program control, and the length of timing is generally established with reference to a number of clock cycles. A Vref/Bias Circuit 58 generates a stable voltage reference and bias currents for the analog circuits of Input/Output Circuit 30. An ADC/Multiplexer Circuit (ADC/MUX) 60 digitizes analog signals and voltages to provide telemetry and a replacement time-indicating or end-of-life function (EOL). A Power-on-Reset Circuit (POR) 62 functions to initialize the pacemaker 10 with programmed values during power-up, and reset the program values to default states upon the detection of a low battery condition or transiently in the presence of certain undesirable conditions such as unacceptably high electromagnetic interference (EMI), for example.

The operating commands for controlling the timing of the pacemaker depicted in FIG. 2 are coupled by bus 48 to Digital Controller/Timer Circuit 50 wherein digital timers set the overall escape interval of the pacemaker, as well as various refractory, blanking and other timing windows for controlling the operation of the peripheral components within Input/Output Circuit 50. This circuit works hand-in-glove with the microcomputer circuit 32 as will be appreciated by those of ordinary skill in this art.

Digital Controller/Timer Circuit 50 is coupled to sense amplifiers (SENSE) 64 and 67, and to electrogram (EGM) amplifiers 66 and 73 for receiving amplified and processed signals picked up from electrode 24 through lead 14 and capacitor 26, and for receiving amplified and processed signals picked up from electrode 22 through lead 15 and capacitor 75, representative of the electrical activity of the patient's ventricle 16 and atrium 17, respectively. Similarly, SENSE amplifiers 64 and 67 produce sense event signals for re-setting the escape interval timer within Circuit 50. The electrogram signal developed by EGM amplifier 66 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", incorporated herein by reference.

Output pulse generators 68 and 71 provide the pacing stimuli to the patient's heart 11 through output capacitors 74 and 77 and leads 14 and 15 in response to paced trigger signals developed by Digital Controller/Timer Circuit 50 each time the escape interval times out, or an externally transmitted pacing command has been received, or in response to other stored commands as is well known in the pacing art.

In a preferred embodiment of the present invention, pacemaker 10 is capable of operating in various non-rate-responsive modes which include DDD, DDI, VVI, VOO and VVT, as well as corresponding rate-responsive modes of DDDR, DDIR, VVIR, VOOR and VVTR. Further, pacemaker 10 can be programmably configured to operate such that it varies its rate only in response to one selected sensor output, or in response to both sensor outputs, if desired. Many other features and functions of pacemakers may be incorporated without going beyond the scope of this invention.

In FIGS. 1a and 1b, in which a marker channel diagram 90 and time associated surface ECG 91 are shown, the terms PVARP, PVAB, TAB, TARP and (S and P)AV are visually illustrated. They are defined in text in the background section above. It is useful to also observe that the second "QRS complex" QRS2(91) is wider than the first, due, we believe, to the fact that it is paced as opposed to "natural".

Adaptive Search AV algorithm

This algorithm generally adapts the AV interval to lengthen where the patient is capable of AV conduction and to shorten otherwise. In the case of a HOCM patient, the adaptive AV search should not be used since its purpose is to promote natural conduction to the ventricle rather than to maintain an artificially early ventricular pacing therapy as is used for the HOCM patient.

There are several ways to pick initial values for the AV interval to be used by the microcomputer circuit 32 of FIG. 2. If there is AV conduction in the patient, a sensed interval value from the P wave to the QRS complex can be used. If not, a value may be programmed in or set.

Two general themes run through these algorithms for setting appropriate AV values; they should allow for detection of natural ventricular events and support intermittent AV block.

Figure 3:
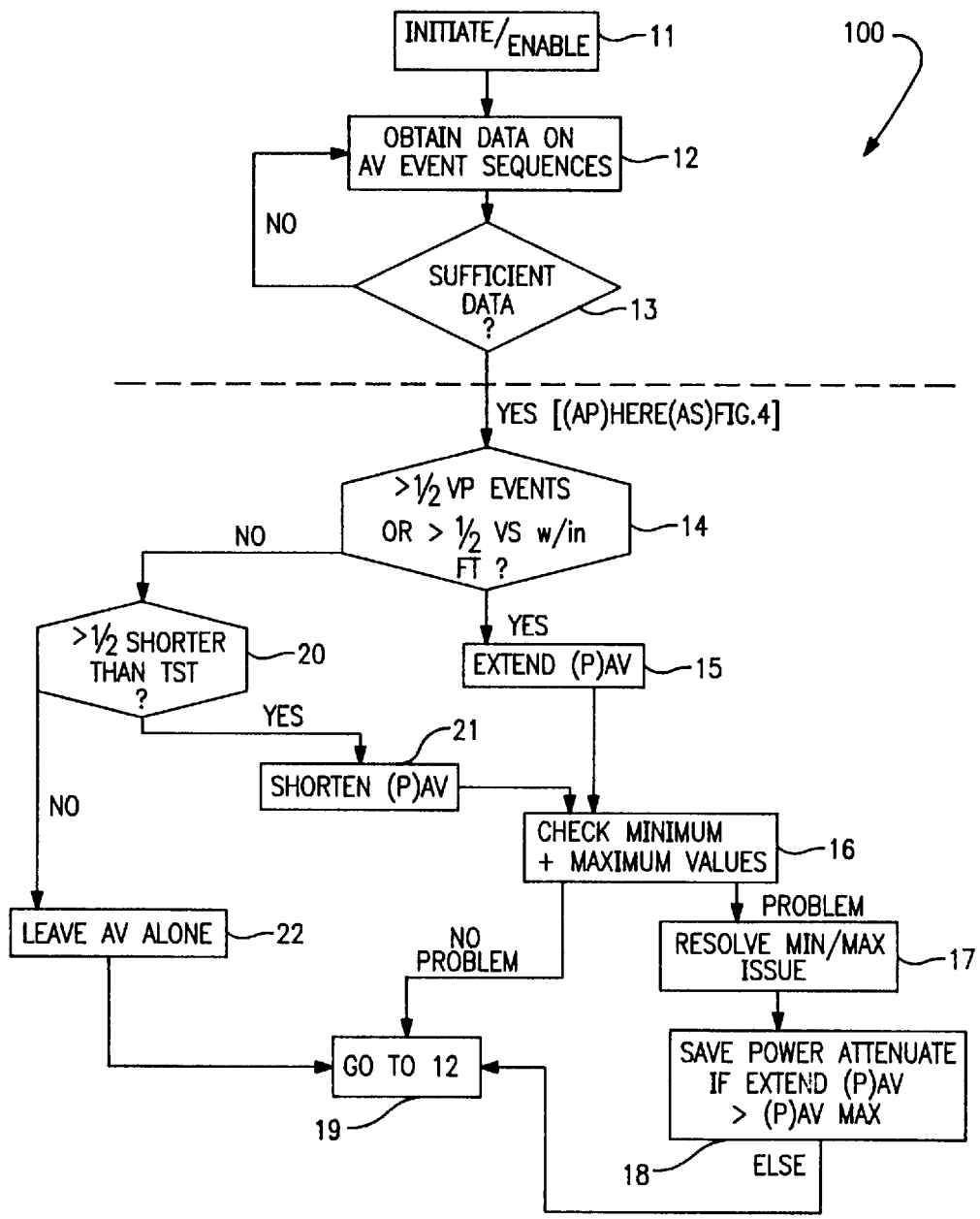
FIG. 3 is a flow chart of the adaptive AV search algorithm in accord with a preferred embodiment.

Referring now to FIG. 3, the first step is to enable the algorithm in step 11, assuming or determining initial values for the AV intervals. Running the pacemaker on these values in step 12, the pacemaker collects data or runs for a number of AV event sequences until the decision at step 13 is satisfied. (To satisfy step 13, no event cycles that end in a safety pace are counted. A "Safety Pace" is a pacing pulse that is triggered by a ventricular sense which occurs within a set period, in preferred embodiments, 110 ms of an atrial pace. The pacemaker thus delivers a ventricular safety pace at 110 ms AV interval. In the event the ventricular sense was crosstalk, that is, sensing of the atrial pace energy in the ventricle, this provides pacing support in the ventricle. If it was a true ventricular event (R-wave), the ventricular pace will be close enough to the R-wave to land in cardiac refractory tissue and not capture the heart. The algorithm will not count safety paces so as to ignore the ventricular senses that trigger safety paces since we don't know if they were really R-waves. The algorithm will also ignore all data from heartbeats during which the AV interval was shortened to preserve a high 2:1 block point. In other words, those beats that cause the automatic PVARP algorithm to set the SAV shorter because the PVARP is longer than the patient's retrograde conduction time are ignored. This is described with reference to FIG. 6 below, step 211.)

Then there are two alternatives. In the simpler of two preferred algorithms, no distinction is made between AV sequences that start with AP or AS, but in the other it matters because two values for the AV interval are kept updated. In that case there is a PAV and an SAV, as defined in the background section above. In the simpler case, only one value of AV interval is updated and it is shared between a base SAV value and a base PAV value, both kept by the pacemaker. In other words, a single updated value is added to two base values.

Starting with the description of single AV interval value only algorithm, when there is sufficient data, the program moves to step 14, where it makes a determination of whether more than one half the event cycles end in either a VP or a VS within Fusion Tolerance (FT). If this determination is true, the AV interval value is lengthened (step 15), if not, a second determination is made in step 20. Step 21 shortens the AV interval if it was determined in step 20 that more than one half of the VS-ended event cycles in the collected data are shorter than (i.e., occur before)the Too Short Tolerance (TST) point.

In other words: If more than ½ of the beats are VP or VS within Fusion Tolerance, extend the AV.

If more than half are VS events that occur at an interval shorter than "Too short Tolerance" the AV delay is shortened (this prevents a 1-way algorithm, shortening the AV when conduction times are shorter than the AV interval value.

If neither criteria is met, zero out the counters (step 22) and leave the AV as programmed(step 19). (Typical values for fusion tolerance (FT) would be 30 ms before the VS, and too short tolerance (TST) would be 60–70 ms.)

The next thing this algorithm does is to check if the AV interval is too long or too short(step 16). These values are set by the manufacturer in the preferred embodiment devices. A block 17 is included in the figure to suggest that the value could be reset to the minimum or maximum value either after the lengthening or shortening is done or that the algorithm could hold the value till resolution of step 16.

Only if we satisfy the first rule to extend the AV, and want to extend the AV, but we would exceed the maximum AV allowed, will the algorithm go into a new search mode to determine whether to continue this search AV algorithm and if so at what extended intervals. Generally this is accomplished by using progressively longer search delay times— starting at for example, 1 hour, and doubling each time until a maximum of 16 hours, and then turning the search for an appropriate AV interval off altogether because there is sufficient proof of natural conduction. Alternatively, the feature could turn itself off entirely if a number of times we searched to the maximum AV and did not discover conduction.

This then is the currently preferred form of the search AV algorithm. In order to understand it fully two terms still need to be defined:

Fusion Tolerance(FT)—this is a period of time BEFORE the ventricular pace. We want to avoid senses that occur very close to when we plan to pace the ventricle since sensing might occur just a little too late, and result in unnecessary pacing in the ventricle. So, if we are sensing close to when the VP would occur, we extend the AV interval to push the VP away and reduce the chance for unnecessary VPs. Too Short Tolerance(TST). This is a defined time period within the AV interval closer to the AP or AS event. If the PR Interval(the time from a Pwave to an Rwave) lengthens, then we extend the AV interval, and then the PR interval shortens, the AV interval may get "stuck" at this long value. Senses that occur so soon in the AV interval as to occur before the TST suggest that the AV interval can be shortened, without risk of initiating unnecessary Ventricular Pacing.

Figure 4:
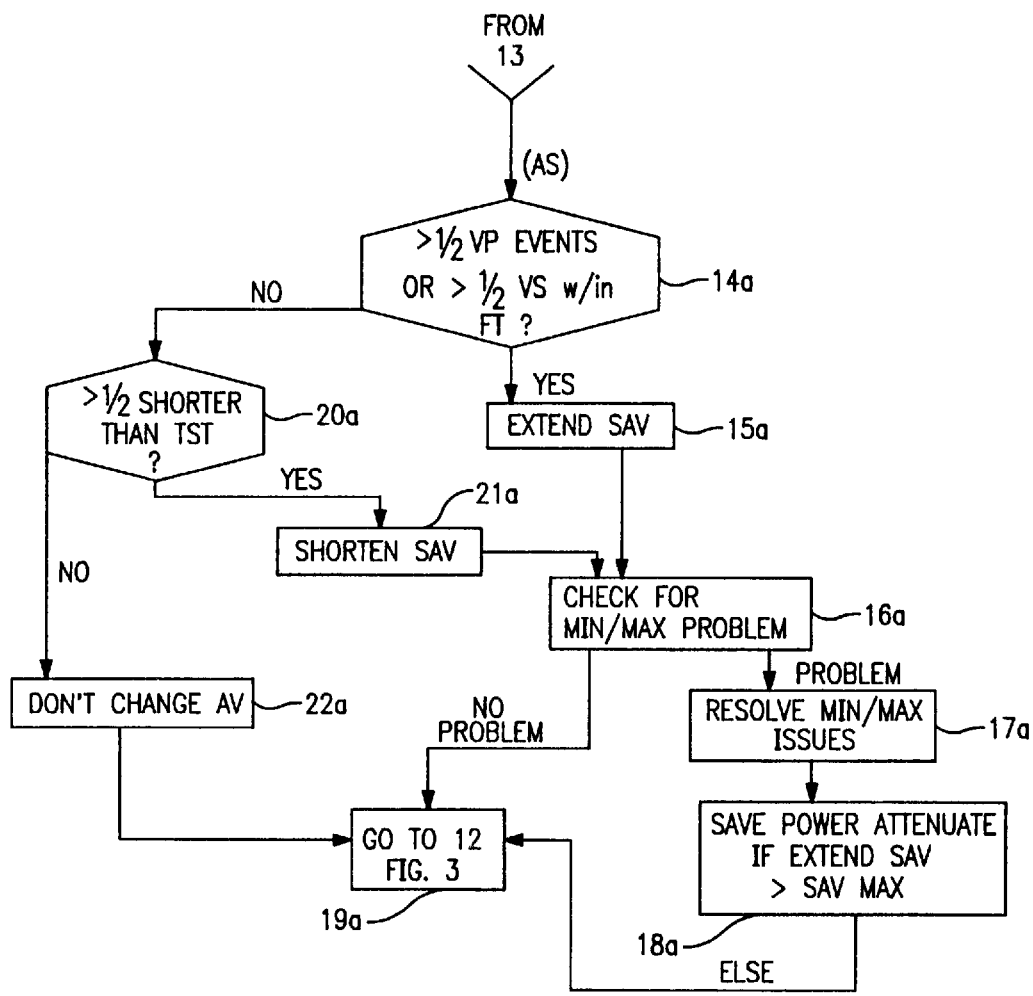
FIG. 4 is a continuation of the flowchart in FIG. 3 for a preferred embodiment.

In FIG. 4 the algorithm 100 is modified below the dotted line to accommodate two AV intervals. Taken together with FIG. 3 where indicated this provides a complete flow chart for this form of the preferred embodiment algorithm. In other words, in FIG. 3 block 15 the activity is to EXTEND PAV, rather than to EXTEND the AV interval value, and so on, throughout the diagram. Thus if the first 16 AV event cycles have a majority that start in AP events, the branch into FIG. 3, step 14 is taken, but if the majority of these 16 cycles are initiated with AS events, the branch to 14a in FIG. 4 is taken. In this way the SAV values and PAV values are maintained independently.

In general it should be noted that sixteen is not a necessary number for the number of data cycles to satisfy step 13, nor is it necessary that a simple majority be used for making the later determination, however, given the constraints of power, time and memory in the modem pacemaker, these seem preferred values. Values for FT in the preferred embodiment is roughly 16 milliseconds(msecs) and for TST, roughly 40 msecs, although the reader may prefer other similar values without abandoning the ambit of this invention. Steps 21 and 21a shorten their AV/SAV/PAV intervals by 7.8125 msecs, and 15 and 15a lengthen their AV/PAV/SAV intervals by 15.625 msecs, although obviously different values could be used if desired. In the preferred embodiments, it seems more sensible to lengthen quicker than shorten, in order to more quickly find VS events. Future users of this algorithmic invention may disagree, and certainly the time of the pacemakers internal clock and other factors will play into decisions on exact time values to use. Also the method of storing the SAV and PAV may vary. There could be a separate value for both kept entirely independently or they could start with the same AV value and the extend and shorten steps could simply add or subtract an offset. In the algorithm form that does not keep a separate SAV and PAV, the pacemaker can establish them as separate values by keeping a start value of different magnitudes for each and adding or subtracting the value of the single offset from that start value. The start values could be, for example, 120 msecs for the SAV and 150 msecs for the PAV. IN this scheme, they would move in tandem, but always be separated by 30 msecs.

Figure 5:
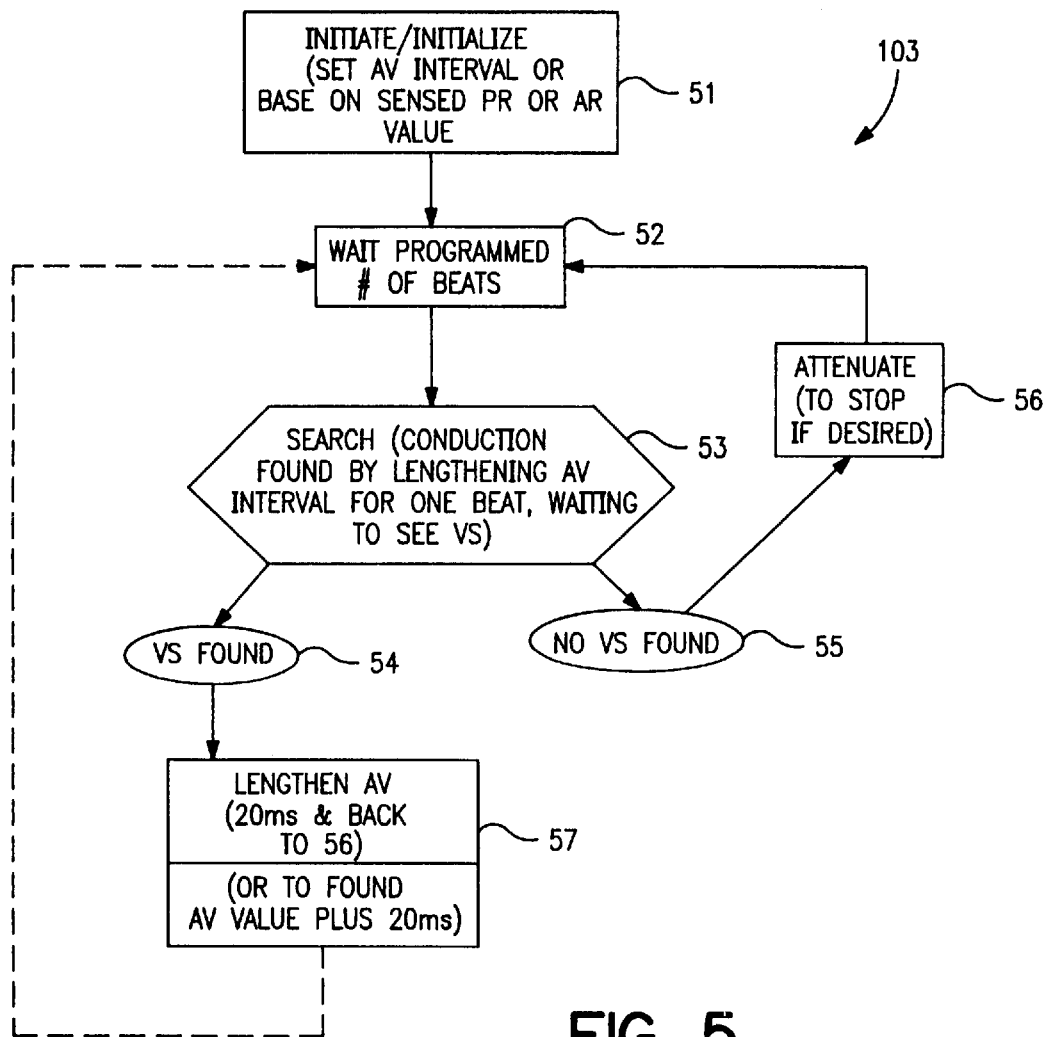
FIG. 5 is a flow chart of another form of the algorithm of FIGS. 3 and 4.

A more general preferred algorithm for search AV is described with reference to FIG. 5 in which the algorithm 103 Starts with some initial values in step 51. On the first round step 52 may be skipped, but generally it will wait a programmed number of beats before moving to the search for VS events in step 53. If a VS is found by extending the AV interval and sensing one during the search beat taken in step 53, this algorithm moves on to step 57, in which the pacemaker kept value of the AV interval is updated. There are several ways to do this, the easiest being to pick a value such as 20 msecs and add it to the current AV value. Another would be to use the sensed AV from the beat taken in step 53 and add 20 msecs to it. In either event after step 57 the program should return to step 52.

When the search step 53 does not find a VS (55), the preferred embodiment goes through an attenuation routine in step 56, just like the attenuation routine in step 17/17a of FIGS. 3 and 4.

Preferred values for Minimum times for AV would be around 50 milliseconds(msecs) and for a Maximum value generally around 250 msecs.

Automatic PVARP

The PVARP has two main purposes in the pacemaker. First it protects from retrograde atrial events being sensed by the pacemaker and starting AV rhythms inappropriately. Otherwise the resulting rhythm will be a "Circus movement or "Endless loop" tachycardia. If the PVARP length is longer than the patient's VA conduction time this rhythm cannot occur. Secondly the PVARP controls the range of rates the patient can synchronize to. Add in the AV period to the PVARP yields the Total Atrial Refractory Period (TARP) When the atrial rate exceeds this value every other atrial event will be tracked to the Ventricle, producing a 2:1 block. It is preferred to have a smaller TARP than the programmed upper tracking rate interval. This would provide a period of Wenckebach operation where the pacemaker remains synchronous to the atrial events but never paces faster than the upper tracking rate. This results in a dropped beat about every 4th beat or so because of lengthening AV intervals. However where the AV interval is manipulated as described above, TARP size becomes dynamic, changing every time SAV (or the AV interval) is shortened. Other operations could also cause the SAV to shorten, such as HOCM pacing therapy etc. In any event, if the TARP is lengthened too far, such that it is greater than or equal to the upper rate interval, the above described Wenckebaching operation will not occur.

To explain in other terms, it should first be recognized that an upper rate is often set to help the patient avoid an ischemic condition which would occur if the intrinsic rate were to be followed. This can occur because of a diseased condition in the patient's heart, or in other words, because the heart is incapable of operating at the rates the body wants it to. Generally, the physician will set the upper rate to something he feels the patient's heart can handle. Since the atrial rate may go beyond that, the Wenkebaching that occasionally drops a ventricular pace is a hemodynamicly reasonable compromise to the heart's assumed diminished capability and the body's intrinsic demand. However, the condition of atrial tachycardia or flutter is not something that should be allowed to develop either, and the pacemaker will assume that a tachy condition has developed when the atrial rate to the ventricular rate is approaching 2:1.

This automatic PVARP is designed to determine what the appropriate 2:1 block point is for a current atrial rate, and allows the pacemaker to be responsive to intrinsic need. It is designed to accommodate changing AV interval size which may be occurring for other reasons (HOCM therapy, for example).

The 2:1 block can be any value above the atrial (A—A) interval value. In the presently most preferred embodiment we have chosen 30 beats per minute (bpm). The atrial interval is one of those values kept by the pacemaker and updated on a regular basis. In our devices we call this the MAI or mean atrial interval, although it is not actually a "mean" value, rather it represents the value determined by our pacemakers to be the true atrial interval value. This MAI value is used to determine if a tachyarrhythmia or flutter is occurring in the atrium, and to follow the intrinsic rate, among other things Thus if the 30 bpm we have chosen is added to the MAI of, say, 100 bpm, and the current A—A interval indicates that the intrinsic rate is greater than or equal to 130 bpm, our pacemaker determines that a tachy condition is occurring. In other words, the 2:1 block point has been reached or exceeded.

The algorithm for figuring this out is described with reference to FIG. 6. It works generally as follows:

The value "Target 2:1 block" is established by the following rules:

Step 1: add 30 bpm to the MAI.

Step 2: if greater than 100 bpm use (30+MAI)bpm else use 100 bpm.

Step 3: use the lesser of the value from Step 2 or (35 bpm+Upper Rate)

This gives us a 2:1 point bounded by 100 bpm and Upper rate+35 bpm, and allows it to move up with increasing intrinsic rate.

It should be noted that Current 2:1 block is the operating SAV+operating PVARP. (Operating" means the values could be set by some other feature—Adaptive AV, HOCM AV, Rate Adaptive AV, etc.)

Figure 6:
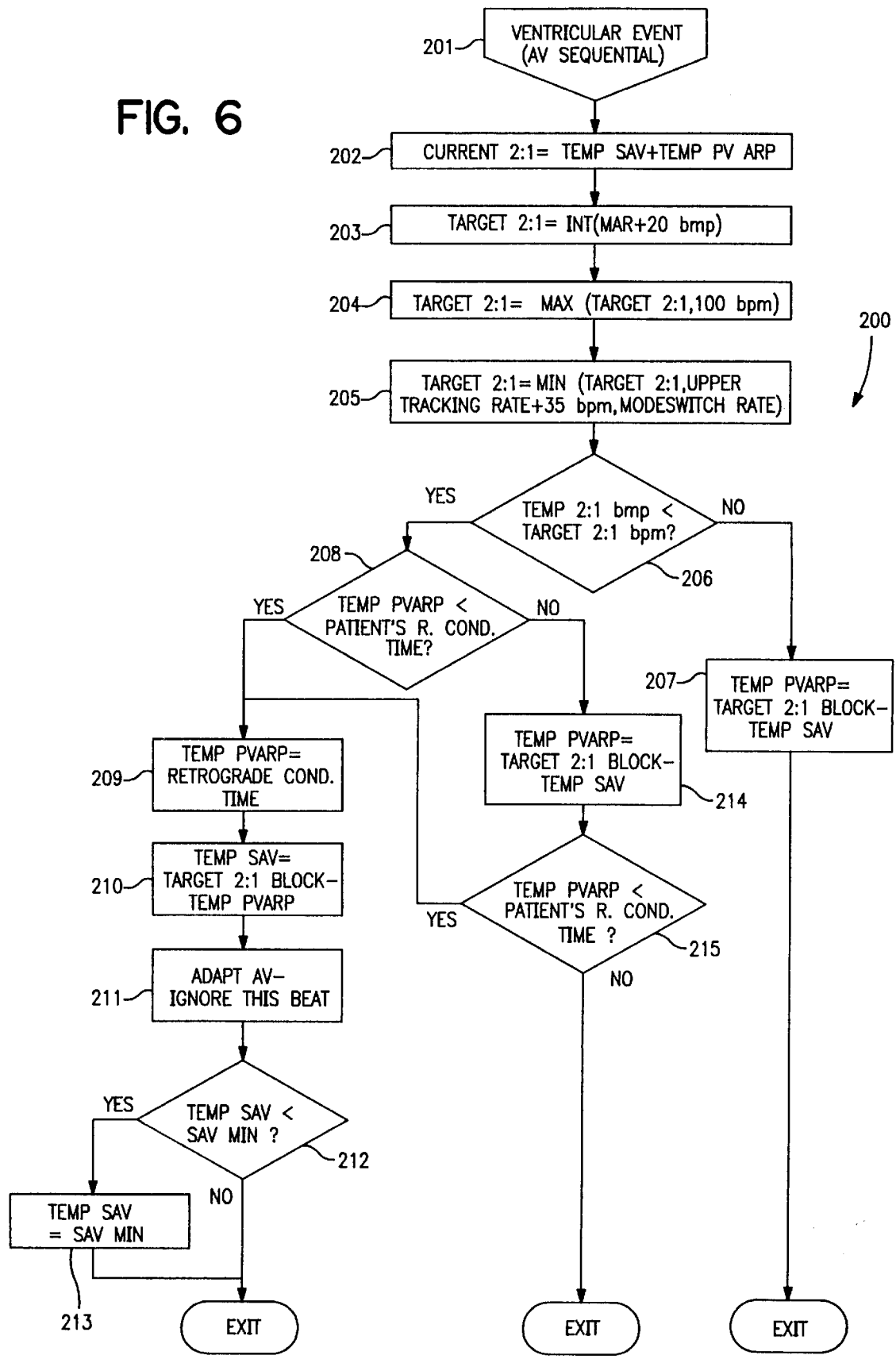
FIG. 6 is a flow diagram of the Automatic PVARP adaptation algorithm in accord with a preferred embodiment.

In FIG. 6, the automatic PVARP algorithm 200 starts with the occurrence of an AV sequential ventricular event(step 201). The Current 2:1 block point is set(Step 202) equal to the sum of the temp SAV value and the temp PVARP values. In other words the program is initialized with the current values. The next step 203 sets the Target 2:1 equal to the true atrial interval (current MAI or MA"R" for Rate). In the following two steps the sorting to find the correct 2:1 value to use is done. The step 204 value picks the maximum between the value from step 203 and 100 bpm. Then step 205 picks the minimum from between that and the upper tracking rate plus the offset of 35 bpm.

In step 206 the algorithm decides whether the temporary 2:1 is less than the target 2:1 established in step 205. The temporary 2:1 was either the initial value or the one set the last time through this algorithm.

If temp 2:1 is not less than Target 2:1, the new value for PVARP is set at the Target 2:1 minus the current operating SAV interval rate value. In this case the program can then exit and wait for the next ventricular event.

On the other hand if the answer to the question of 206 is yes, another determination must be made, that is, is the current PVARP value less than the patient's retrograde conduction time? (this is a number either set by the pacemaker manufacturer or the physician). If yes, the PVARP value is increased to be at least as long as that retrograde conduction time (step 209) and the SAV value is set to the value of the Target 2:1 minus this PVARP value. The next step 211 is a way for this algorithm to function with the algorithm of FIGS. 3 and 4 above. In other words, if we have gone down this step 209 branch, this ventricular beat should be ignored by the adaptive AV search. The simplest way to accomplish this is to add a flag bit to the data kept for this beat by the AV search algorithms, this flag being set by this Automatic PVARP algorithm. Other methods and structures will come readily to mind for the reader of ordinary skill without exceeding the ambit of this invention.

In step 212, the algorithm decides if the SAV value determined in step 210 is less than the minimum SAV and if so resets it to the minimum SAV value(step 213), and in either case exits.

Going back to step 208, if a no decision was taken, the PVARP value is set to the Target 2:1 minus the SAV value in step 214, then if this is less than the patient's retrograde conduction time, again the step 209 branch is taken. Otherwise the program can exit here.

Thus, PVARP is set equal to the difference between the current SAV and the target 2:1 block point. Normally, then, Current TARP=Target TARP. Also, PVARP cannot be set shorter than MINIMUM PVARP. So, Current TARP could be greater than Target PVARP. If that happens, we want to shorten the AV interval so that Current TARP=Target TARP. We can also shorten the SAV down to a defined minimum in this attempt.

This gives us a picture like that of FIG. 7, in which the intrinsic atrial rate as expressed in the MAI is shown in dark squares, and the 2:1 block point is shown in open squares.

Some example numbers which will go through the algorithm described in FIG. 6 follow:

MAI=90 bpm

SAV=150 ms

Minimum PVARP=200 ms

The target 2:1 block point would be 90+30 bpm=120 bpm, or 500 ms. Subtracting the SAV of 150 ms from this value gives PVARP of 350 ms, well above the minimum. So Current TARP=Target TARP right away.

MAI=90 bpm

SAV=200 ms,

Minimum PVARP=350 ms.

Again the Target 2:1=120 bpm, or 500 ms. Subtracting the SAV would give a PVARP of 300 ms, which is shorter than the minimum allowed. So PVARP can only go down to 350. Current TARP=550, different from the Target TARP of 500 ms. this will require the SAV to shorten by 50 ms or down to the minimum allowed) so Target=Current. the final values would be SAV=150, PVARP=350.

Many variations on the inventive concepts taught herein can be easily imagined, by for example shifting the values (like 30 bpm) a few beats in either direction. Nevertheless, these are believed to be within the scope of this invention which is only limited as set forth in the following claims.

We claim:

1. A method to determine if AV conduction is occurring so as to eliminate a substantial number of unnecessary ventricular paces wherein a pacemaker for performing such method has a stored and updatable value for an AV interval upon which it makes a determination of when to deliver a next ventricular pacing pulse, said method comprising the steps:

storing a predetermined number of AV event cycles' timing values, providing a first testing step in one heart beat cycle in a set of successive heart beat cycles to determine whether a Ventricular Sense (VS) event would occur after a scheduled Ventricular Pace(VP) by extending the AV interval in a successive heart beat cycle so as to allow said VS to occur in a first lengthened AV interval, then determining if said VS occurred after applying the first lengthened AV interval, and then, lengthening the first lengthened AV interval used to determine the time to generate a VP if said VS did occur within said first lengthened AV interval.

2. The method set forth in claim 1 wherein if the AV interval is not caused to be lengthened during said lengthening step, attenuating a value for determining how often said first testing is repeated with respect to time.

3. The method of claim 1 wherein said testing step comprises determining whether more than a predetermined amount of said stored event cycles either ended in a VP event or a VS event within Fusion Tolerance (FT).

4. The method of claim 3 wherein said testing step further comprises determining whether more than said predetermined number of stored event cycles ended in VS that were shorter than Too Short Tolerance (TST), and if so shortening the AV interval value kept by the pacemaker, but if not and less than or the same number of stored event cycles ended in a VP or a VS within FT, then, leaving the current value of said pacemaker maintained AV interval as is.

5. The method of claim 4 further comprising the step of determining whether the value for AV interval kept by the pacemaker is within range of predetermined max and min values.

6. A method as set forth in claim 5 and further comprising the step of attenuating a value for determining the amount of times said search AV algorithm is implemented per a given time period.

7. An implantable dual chamber pulse generator (IPG) capable of determining if AV conduction is occurring so as to eliminate a substantial number of unnecessary ventricular paces wherein said IPG maintains in memory an updatable value for an AV interval upon which value said IPG makes a determination of when to deliver a next ventricular pacing pulse, said IPG further comprising:

means for determining whether a Ventricular Sense(VS) event would occur after a scheduled Ventricular Pace (VP) by causing a temporary extension to the AV interval value so as to allow said VS to occur within a heartbeat cycle in which said extension was applied, means for lengthening by successive increments or calculated values said maintained AV interval if said VS did occur within said lengthened AV interval and means for storing values for Sense AV intervals and Pace AV intervals, such that said means for lengthening said AV interval value allows for the adding to or subtracting from said stored values for said Sense AV interval and for said Paced AV interval such that the stored and updatable value for the AV interval is added to or subtracted from said Pace AV interval value after an atrial pace but added to or subtracted from said Sense AV interval value after an atrial sense.

* * * * *